(12) United States Patent
Sugiyama et al.

(10) Patent No.: US 7,666,663 B2
(45) Date of Patent: Feb. 23, 2010

(54) CORRECTION METHOD FOR THE DISTRIBUTION OF QUANTITY OF LIGHT AND BIOCHIP-READER

(75) Inventors: Yumiko Sugiyama, Musashino (JP); Takeo Tanaami, Musashino (JP)

(73) Assignee: Yokogawa Electric Corporation, Tokyo (JP)

( * ) Notice: Subject to any disclaimer, the term of this patent is extended or adjusted under 35 U.S.C. 154(b) by 263 days.

(21) Appl. No.: 10/931,962

(22) Filed: Sep. 2, 2004

(65) Prior Publication Data

US 2005/0142579 A1    Jun. 30, 2005

(30) Foreign Application Priority Data

Dec. 24, 2003  (JP)  ............... 2003-426153

(51) Int. Cl.
  *C12M 1/34* (2006.01)
  *C12M 3/00* (2006.01)
  *C12Q 1/68* (2006.01)
  *G01N 33/53* (2006.01)
  *G01N 15/06* (2006.01)

(52) U.S. Cl. .................. 435/287.1; 435/6; 435/7.1; 435/287.2; 422/68.1

(58) Field of Classification Search .............. 435/6, 435/91.1, 183, 283.1, 287.1, 287.2, 7.1; 422/50, 422/68.1
See application file for complete search history.

(56) References Cited

U.S. PATENT DOCUMENTS

2003/0030797 A1   2/2003  Palladino et al.
2003/0105195 A1   6/2003  Holcomb et al.

FOREIGN PATENT DOCUMENTS

| JP | 2003-28799 | 1/2003 |
|---|---|---|
| WO | WO 01/55964 A2 | 8/2001 |
| WO | WO 01/59503 | 8/2001 |
| WO | WO 03/000300 A1 | 1/2003 |
| WO | 2004/101354 | 2/2004 |
| WO | WO 2004/023117 | 3/2004 |

OTHER PUBLICATIONS

Y. Zhai et al. "Quantitative determination of the proportion of microtubule polymer present during the mitosis-interphase transition", Journal of Cell Science 107, pp. 881-890 (1984).

*Primary Examiner*—Frank W Lu
(74) *Attorney, Agent, or Firm*—Westerman, Hattori, Daniels & Adrian, LLP

(57) ABSTRACT

The present invention is characterized by the following points:

In a biochip reader used for reading a measurement sample image by light beam irradiation, a correction method for the distribution of quantity of light which is devised to remove the influence of shading for the whole image and such a biochip reader can be realized by correcting non-uniformity in said quantity of light in light beam irradiation by dividing the quantities of light of pixels in a measured image obtained from the measurement of a measurement sample by a distribution of quantity of light in an image obtained from the measurement of a uniform fluorescent plate that presents a uniform fluorescent light distribution, the positions of pixels in the measured image being correspondent to those in the image obtained through the above uniform fluorescent plate measurement.

4 Claims, 4 Drawing Sheets

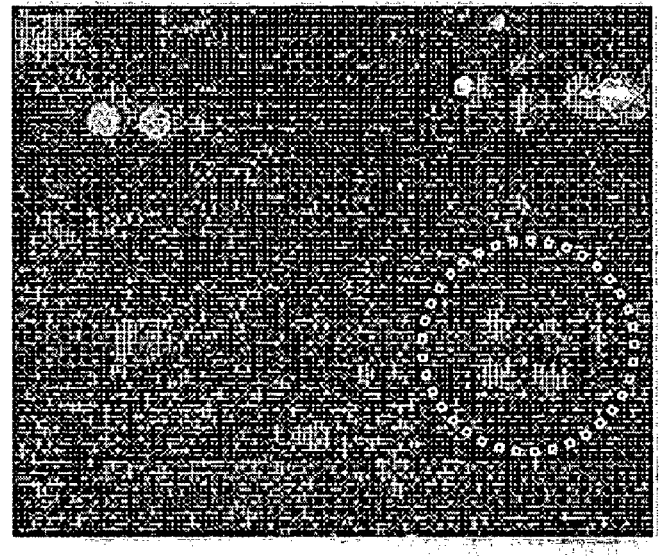
FIG.2C Sample:After correction
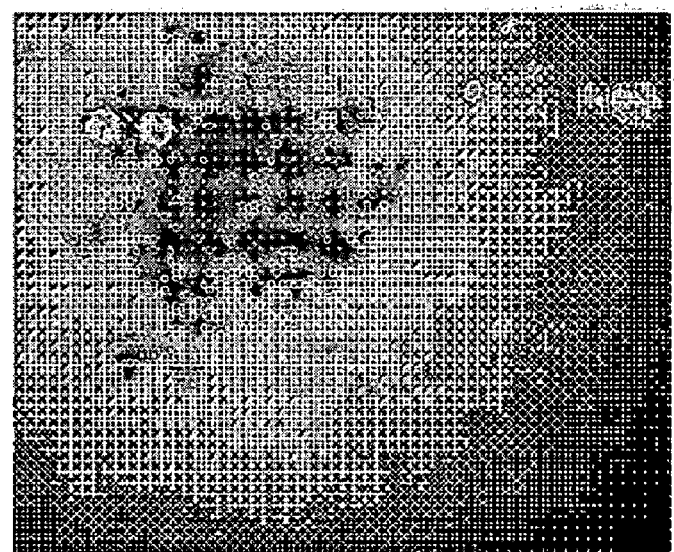
FIG.2B Sample:Before correction
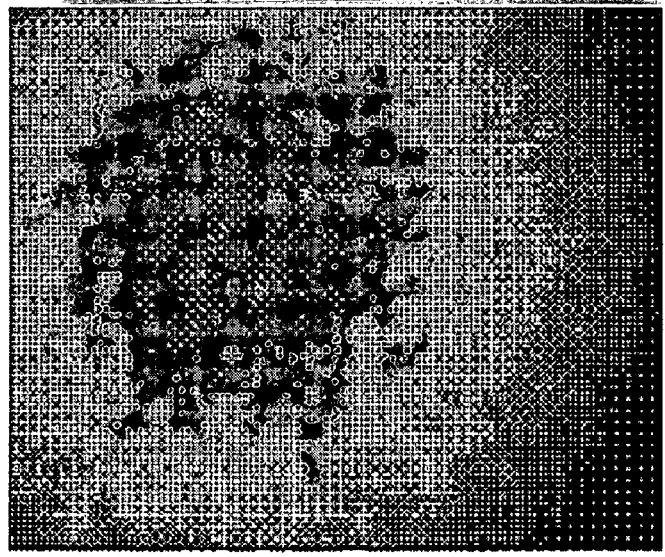
FIG.2A Uniform fluorescent plate

A—· ·—A

Correction distribution

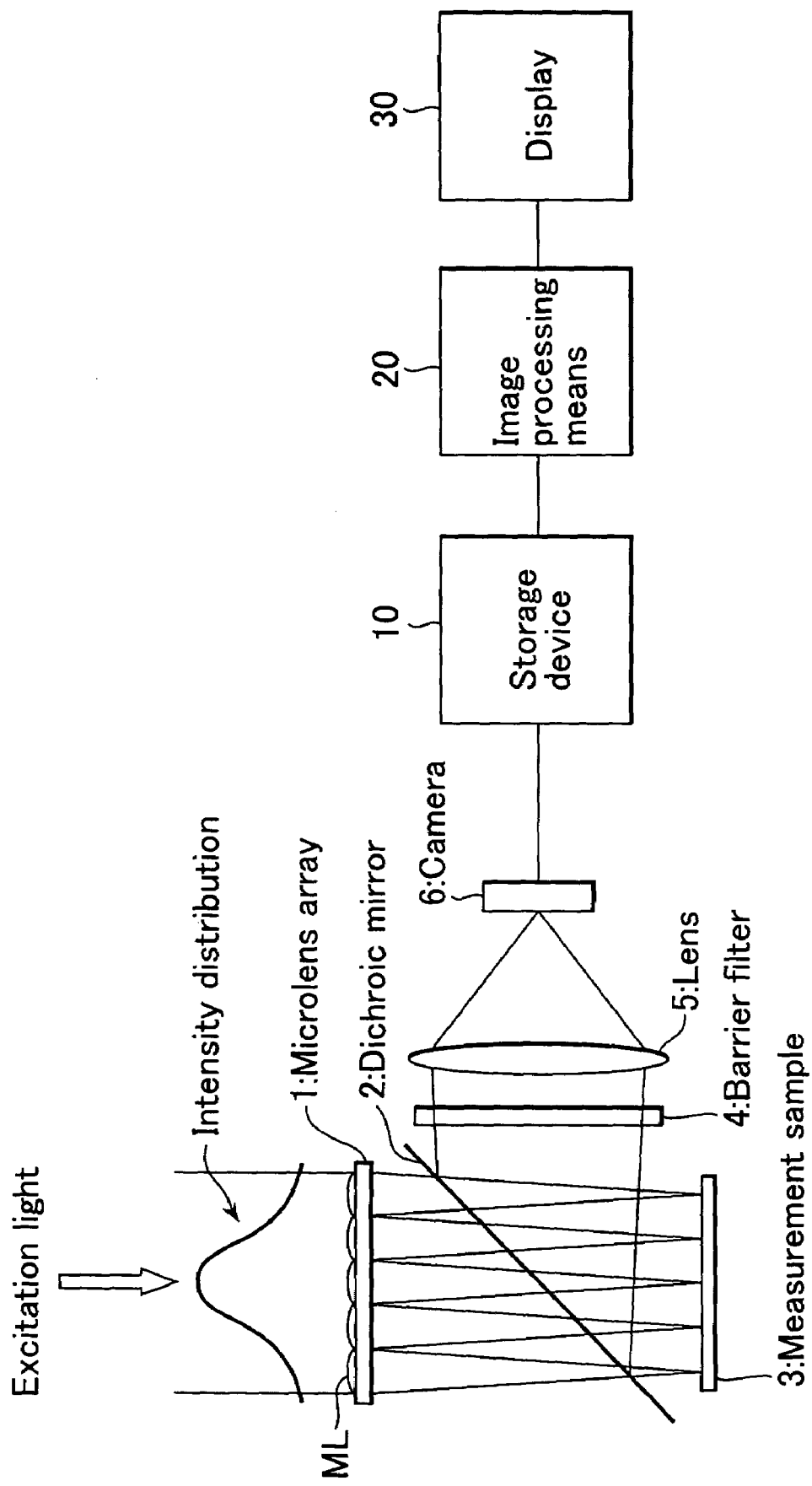

CORRECTION METHOD FOR THE DISTRIBUTION OF QUANTITY OF LIGHT AND BIOCHIP-READER

BACKGROUND OF THE INVENTION

1. Field of the Invention

The present invention relates to a biochip reader and also to a method for correcting the influence of intensity distribution (shading) of a light source (excitation light).

Specifically, the influence of this shading is large in the scan-less type biochip reader in which a wide biochip range is measured simultaneously with a plurality of light beams.

2. Description of the Prior Art

This kind of scan-less type biochip reader is well known from the past (for example, refer to Patent Document 1). FIG. 1 is a configuration drawing indicating the essential part of an example of the scan-less type biochip reader described in Patent Document 1.

In FIG. 1, laser light (excitation light) emitted from a light source becomes parallel light and is incident to microlens array 1. Microlens array 1 is an arrangement of a plurality of microlenses (ML) and excitation light converged respectively by each microlens (ML) irradiates measurement sample 3 after transmitting dichroic mirror 2. Measurement sample 3 is constructed so that a plurality of cells (sites) is arranged in a two-dimensional manner and a sample is poured in each cell (site).

Fluorescent light from each sample is reflected by dichroic mirror 2 and is incident to lens 5 via barrier filter 4. Barrier filter 4 has the effect of acting to transmit fluorescent light from measurement sample 3 but to attenuate the excitation light reflected by measurement sample 3, and is used to eliminate the background light of a sample image. A sample image focused and formed by lens 5 is captured by camera 6.

According to such a configuration, a plurality of cells (sites) on a biochip can be measured at the same time with a scan-less method in which excitation light is not scanned.

[Patent Document 1]
Gazette for Japanese Laid-open Patent Application No. 2003-28799 (p. 6, FIG. 13)

However, in such conventional biochip readers, the distribution of excitation light intensity becomes the distribution of excitation light intensity on the measurement plane of a biochip without change and thus excitation light intensity is different at each site even on the same chip.

Accordingly, conventional biochip readers have the following problems:

(1) There are portions on a biochip where excitation light is strong and portions on the same biochip where excitation light is weak. This affects the amount of fluorescent light emission. In particular, differences between these strong and weak light intensities are extremely large for scan-less type readers.

(2) If the quantities of light are simply corrected using a certain factor, they become unknown in the case where the absolute quantity of light calibration system using a power meter traceable to national standards is used.

(3) If the quantities of light are simply corrected using a certain factor, pixels may be easily saturated or the tones over the whole pixels of images may be lowered to the span.

SUMMARY OF THE INVENTION

The objective of the present invention is to solve such problems and thus to offer a correction method for the distribution of quantity of light, which removes the influence of shading of the whole image by measuring a reference quantity of light distribution image of the excitation light using a uniform fluorescent plate that presents a uniform fluorescent light distribution and by dividing the measured sample image by the aforementioned reference quantity of light distribution image to correct non-uniformity of a quantity of light, and to offer a biochip reader using the above described method.

BRIEF DESCRIPTION OF DRAWINGS

FIG. 1 is a configuration drawing indicating the essential part of an example of conventional scan-less type biochip readers.

[FIGS. 2A, 2B and 2C]

FIGS. 2A, 2B and 2C show drawings for illustrating a correction method for the distribution of quantity of light concerning the present invention.

FIGS. 3A and 3B show drawings for illustrating the distribution of light intensity and the distribution of quantity of light for a scan-less type reader.

[FIG. 4]

FIG. 4 is a configuration drawing indicating the essential part of an embodiment of a biochip reader using the method of the present invention.

DESCRIPTION OF THE PREFERRED EMBODIMENTS

The present invention will be described below in detail using drawings. The procedure for the correction method for the distribution of quantity of light is as shown below. A biochip reader may be either the scan-less type or a scanning type.

(1) First, a uniform fluorescent plate is prepared, that presents a uniform fluorescent light distribution in a range having an area equivalent to a measurement area for a measurement sample. Then a fluorescent image of this uniform fluorescent plate, that is, the reference quantity of light distribution image "a" is measured by irradiating excitation light using a biochip reader. The value (light intensity) of each pixel in this case is given as "$a_i$" ("i" shows the number of pixels and so takes a value 1 to n).

(2) The average tone "$a_{Ave}$" of the above obtained reference quantity of light distribution image "a" is determined, then the light source intensity correction image "a'" is determined by dividing the values of each pixel by this average tone "$a_{Ave}$" [the values of each pixel are represented by "$a'_i$" (i=1 to n)].

This enables a light source intensity correction image, in which the tone of the reference quantity of light distribution image "a" is normalized to 1 and the total energy value is made unchanged as shown in FIG. 2A, to be obtained. In addition, FIG. 2 shows images measured with a scanning type biochip reader.

(3) A measurement sample is measured using a light source of the same intensity distribution in the same biochip reader as mentioned before to obtain a measurement sample image "b" [values of each pixel are "$b_i$" (i=1 to n)] as shown in FIG. 2B.

(4) Next, as shown in equation (1), a corrected sample image "c" [values of each pixel are "$c_i$" (i=1 to n)] is deter mined by dividing the measurement sample image "b" by the above described light source intensity correction image "a'".

$$c_i = b_i \div a'_i \quad (1)$$

According to this correction method, the following effects are obtained:

(1) Normalization of the tone of the light source intensity correction image to 1
   gives no change in the total energy, that is, the total quantity of light energy is maintained, and
   prevents the values of pixels from taking extremely large or small values.

(2) Fluorescent images of sites, which cannot be seen in FIG. 2B due to the lack of uniformity in the distribution of the quantity of light for the light source, become visible by performing correction as shown in the circle at the lower left of FIG. 2C. In other words, highly sensitive measurements are made possible.

Figure 3A:
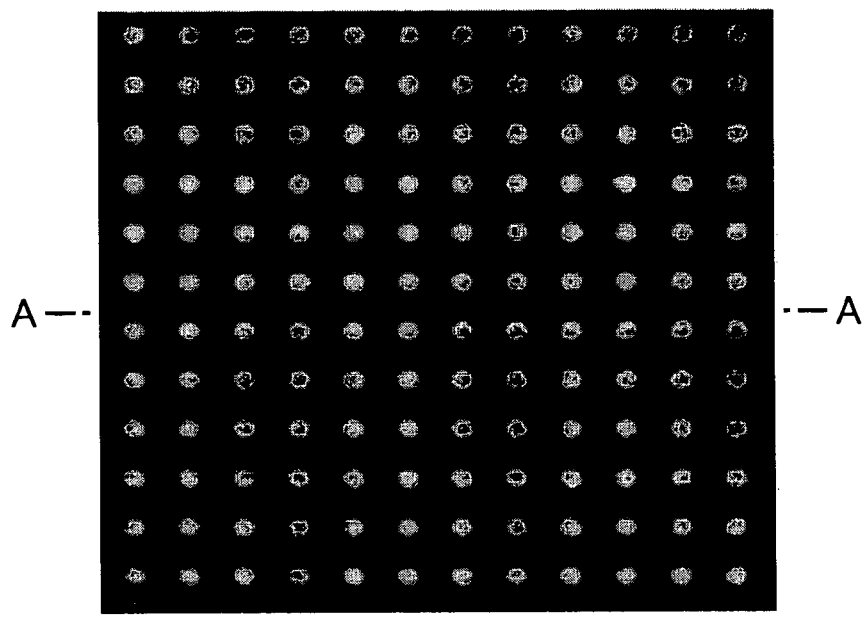
[FIGS. 3A and 3B]
Figure 3B:
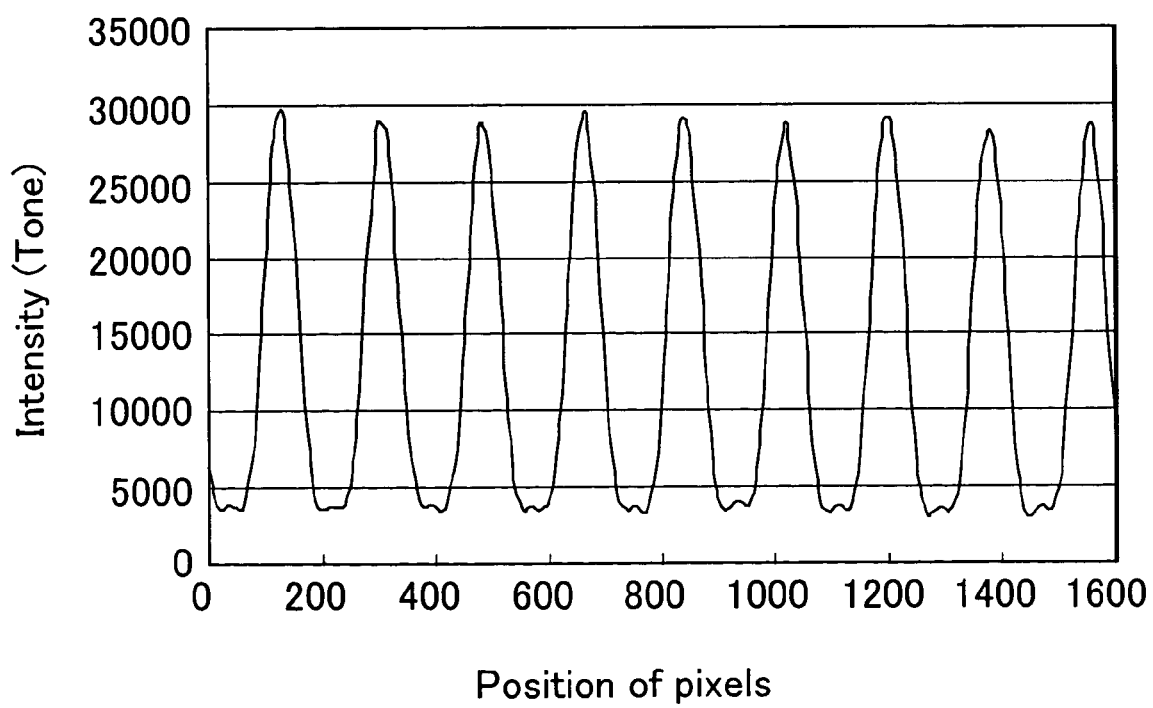

Further, if a biochip reader is of the scan-less type which does not scan a light beam, a far more non-uniform intensity distribution than that in the image shown in FIG. 2B is generated as shown in FIG. 3A. However, the distribution can also be corrected using a similar technique. A corrected light intensity distribution of the sites on the A-A line shown in FIG. 3A is indicated in FIG. 3B.

If a camera for capturing images or the like has an offset x, the value for offset should be subtracted from values of each pixel in advance before performing division as shown in equation (2).

$$c_i = (b_i - x) \div \{(a_i - x) \div (a_{Ave} - x)\} \quad (2)$$

Figure 1:
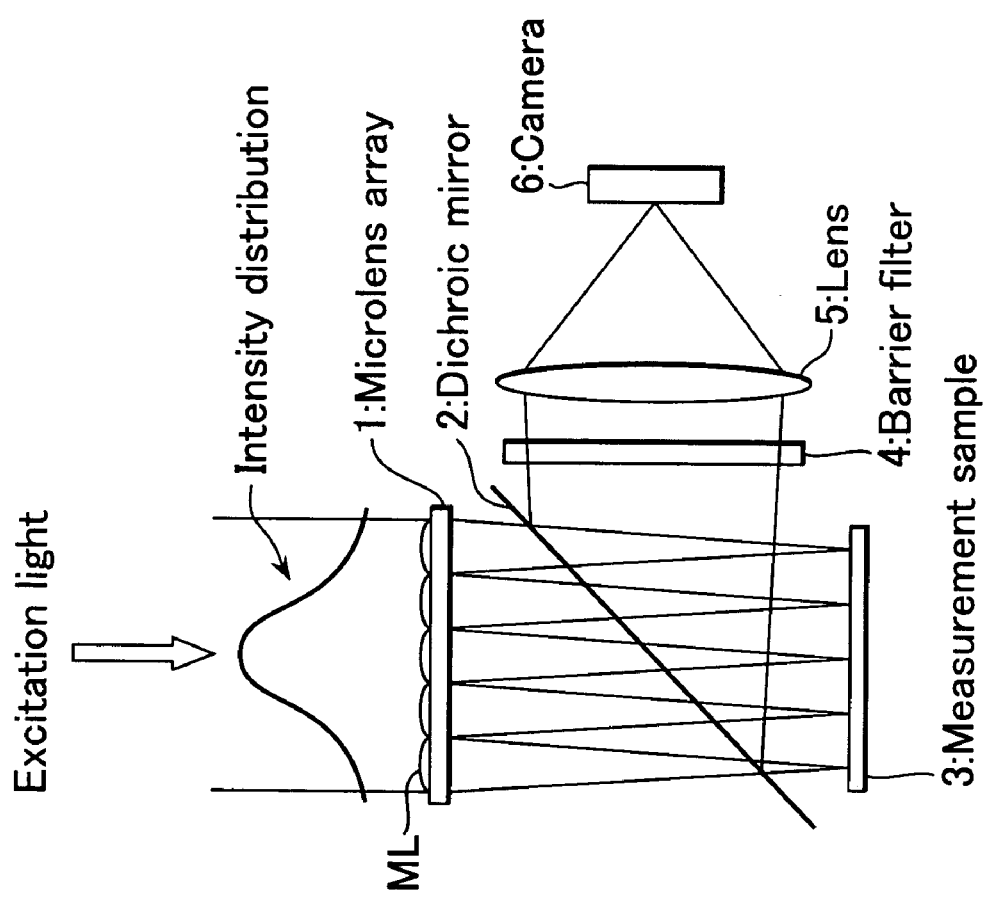
[FIG. 1]

FIG. 4 is a configuration drawing indicating the essential part of an embodiment of a biochip reader for practical use in the method of the present invention. In addition, in FIG. 4, a scan-less type biochip reader is shown, and the same signs as those shown in FIG. 1 are given to the parts identical to those in FIG. 1.

In FIG. 4, storage device 10 stores image data measured with camera 6 included in the capturing means. Image processing means 20 carries out calculation and image processing shown in the above mentioned correction method for the distribution of quantity of light based on image data read from storage device 10. The corrected sample image for the measurement sample obtained is displayed in display 30.

In such a configuration, first fluorescence measurement is done initially by mounting a uniform fluorescent plate in the position of measurement sample 3 and image data of reference quantity of light distribution image "a" obtained with the capturing means, that is, camera 6, is stored in storage device 10.

Next, measurement sample 3 is mounted in lieu of the uniform fluorescent plate and the sample image is measured with camera 6 in the same manner, and image data of that measurement sample image "b" is stored in storage device 10.

In image processing means 20, average tone "$a_{Ave}$" of the total pixels of reference quantity of light distribution image "a" read from storage device 10 is determined, and values of each pixel of the original reference quantity of light distribution image "a" are divided by this average tone "$a_{Ave}$" respectively. The result of this division is given as light source intensity correction image "a'". As described above, light source intensity correction image near 1 is obtained. Subsequently, measurement sample image "b" is divided by the above light source intensity correction image "a'" for each corresponding pixel.

Corrected sample image "c", determined as described above, is indicated in display 30.

In addition, the present invention is not restricted to the above embodiment but may be embodied in other specific forms, changes, and versions without departing from the true spirit thereof.

For example, storage device 10 and image processing means 20 may also be made as an integral configuration, not separate ones.

As apparent from the above description, the following effects are obtained according to the present invention:

(1) A light source intensity correction image, in which the average value is made as 1, is obtained by determining the average tone of an image for a uniform fluorescent plate and by dividing the intensities of each pixel by the average tone. Accordingly, a measured image, in which non-uniformity of quantity of light is corrected, can easily be obtained by dividing the measured image by the above light source intensity correction image.

(2) Since a light source intensity correction image, in which the average value is made as 1, is obtained as described above, it is possible to obtain a light source intensity correction image whose total energy does not change, that is, the total quantity of light energy is maintained.

Further, according to such correction, no pixel values become extremely large or extremely small.

(3) As seen in the circle in the lower left portion of the image shown in FIG. 2C, sites not seen in the image shown in FIG. 2B become easily visible.

What is claimed is:

1. A method of correcting a distribution of a quantity of fluorescent light on a biochip using a biochip reader comprising a camera, the method comprising:

mounting a uniform fluorescent plate in said biochip reader;

emitting excitation light from a light source and irradiating said uniform fluorescent plate thereby producing fluorescent images of said uniform fluorescent plate;

obtaining a plurality of intensity values of fluorescent images of said uniform fluorescent plate by measuring the intensity of each individual pixel of said uniform fluorescent plate with said camera, each of the plurality of intensity values of said uniform fluorescent plate representing the intensity value of one individual pixel of said uniform fluorescent plate;

obtaining an average value of reference quantity of fluorescent light distribution image from said uniform fluorescent plate by averaging said plurality of intensity values of fluorescent images of said uniform fluorescent plate;

mounting a biochip comprising measurement samples in said biochip reader in lieu of said uniform fluorescent plate, said uniform fluorescent plate having an area equivalent to the area comprising said measurement samples on said biochip;

emitting excitation light from said light source and irradiating said biochip, said measurement samples on said biochip being capable of emitting fluorescent light in response to the irradiation with said excitation light;

obtaining a plurality of intensity values of fluorescent images from said biochip by measuring intensity of each individual pixel of said measurement samples on said biochip with said camera, each of the plurality of intensity values of said biochip representing the intensity value of one individual pixel of said measurement samples on said biochip; and obtaining a fluorescent light source intensity corrected sample image value for each individual pixel of said biochip, thereby correcting the distribution of the quantity of fluorescent light on said biochip according to the following formulas:

$$a_i' = a_i \div a_{Ave} \quad (I)$$

$$c_i = b_i \div a_i' \quad (II)$$

wherein $a_i'$ represents a fluorescent light source intensity correction image value for said each individual pixel of said uniform fluorescent plate, $a_i$ represents said intensity value of said each individual pixel of said uniform fluorescent plate, $a_{Ave}$ represents said average value of reference quantity of fluorescent light distribution image of said uniform fluorescent plate, $c_i$ represents said fluorescent light source intensity corrected sample image value for said each individual pixel of said biochip, and $b_i$ represents the intensity value of said each individual pixel of said measurement samples on said biochip, and wherein i represents a number of said each individual pixel of said uniform fluorescent plate and of said measurement samples of said biochip, and has a value of 1 to n.

2. The method of claim 1, wherein said fluorescent light intensity value for said each individual pixel of said uniform fluorescent plate and said average value of reference quantity of fluorescent light distribution image of said uniform fluorescent plate are obtained by a scan-less method in which multiple light beams are irradiated to sites of said biochip in which said measurement samples are disposed.

3. A method of correcting a distribution of a quantity of fluorescent light on a biochip using a biochip reader comprising a camera, the method comprising:

mounting a uniform fluorescent plate in said biochip reader;

emitting excitation light from a light source and irradiating said uniform fluorescent plate thereby producing fluorescent images of said uniform fluorescent plate;

obtaining a plurality of intensity values of fluorescent images of said uniform fluorescent plate by measuring intensity of each individual pixel of said uniform fluorescent plate with said camera, each of the plurality of intensity values of said uniform fluorescent plate representing the intensity value of one individual pixel of said uniform fluorescent plate;

obtaining an average value of reference quantity of fluorescent light distribution image from said uniform fluorescent plate by averaging said plurality of intensity values of fluorescent images of said uniform fluorescent plate;

mounting a biochip comprising measurement samples in said biochip reader in lieu of said uniform fluorescent plate, said uniform fluorescent plate having an area equivalent to the area comprising said measurement samples on said biochip;

emitting excitation light from said light source and irradiating said biochip, said measurement samples on said biochip being capable of emitting fluorescent light in response to the irradiation with said excitation light;

obtaining a plurality of intensity values of fluorescent images from said biochip by measuring intensity of each individual pixel of said measurement samples on said biochip with said camera, each of the plurality of intensity values of fluorescent images from said biochip representing the intensity value of one individual pixel of said measurement samples on said biochip; and obtaining a fluorescent light source intensity corrected sample image value for each individual pixel from said biochip, thereby correcting the distribution of the quantity of fluorescent light on said biochip according to the following formulas:

$$a_i' = (a_{i-x}) \div (a_{Ave} - x) \quad (I)$$

$$c_i = b_i \div a_i' \quad (II)$$

wherein $a_i'$ represents a fluorescent light source intensity correction image value for said each individual pixel of said uniform fluorescent plate, $a_i$ represents said light intensity value of said each individual pixel of said uniform fluorescent plate, $a_{Ave}$ represents said average value of reference quantity of fluorescent light distribution image of said uniform fluorescent plate, and x represents an optical system offset of said camera, $c_i$ represents said fluorescent light source intensity corrected sample image value for said each individual pixel of said biochip and $b_i$ represents the intensity value of said each individual pixel of said measurement samples on said biochip, and wherein i represents a number of said each individual pixel of said uniform fluorescent plate and of said measurement samples of said biochip, and has a value of 1 to n.

4. The method of claim 3, wherein said fluorescent light intensity value for said each individual pixel of said uniform fluorescent plate and said average value of reference quantity of fluorescent light distribution image of said uniform fluorescent plate are obtained by a scan-less method in which multiple light beams are irradiated to sites of said biochip in which said measurement samples are disposed.

* * * * *